United States Patent [19]

Sachse

[11] Patent Number: 5,531,718
[45] Date of Patent: Jul. 2, 1996

[54] TUBE-SHAPED URETER SPLINT

[76] Inventor: Hans Sachse, Lerchenstr. 55, D-90425 Nürnberg, Germany

[21] Appl. No.: 143,113

[22] Filed: Oct. 29, 1993

[30] Foreign Application Priority Data

Oct. 29, 1992 [DE] Germany ............................ 42 36 571.6

[51] Int. Cl.$^6$ ................................................. A61M 37/00
[52] U.S. Cl. ............................................................. 604/280
[58] Field of Search ................................ 604/280, 7, 246, 604/8, 247, 14, 53; 128/DIG. 25

[56] References Cited

U.S. PATENT DOCUMENTS

| | | | |
|---|---|---|---|
| 4,177,814 | 12/1979 | Knepshield et al. | 128/348 |
| 4,553,959 | 11/1985 | Hickey et al. | 128/DIG. 25 |
| 4,657,536 | 4/1987 | Dorman | 604/9 |
| 4,790,809 | 12/1988 | Kuntz | 604/280 |
| 4,828,554 | 5/1989 | Griffin | 604/350 |
| 4,931,037 | 6/1990 | Wetterman | 604/280 |
| 4,968,294 | 11/1990 | Soloma | 604/247 |
| 5,005,732 | 4/1991 | Penn | 222/91 |
| 5,085,635 | 2/1992 | Cragg | 604/96 |

FOREIGN PATENT DOCUMENTS

| | | | |
|---|---|---|---|
| 018179 | 4/1979 | European Pat. Off. . | |
| 351864 | 1/1990 | European Pat. Off. . | |
| 0494732 | 7/1992 | European Pat. Off. | 604/280 |
| 2600259 | 7/1976 | Germany | 128/DIG. 25 |
| 3641107 | 6/1987 | Germany | 604/280 |
| 4028477 | 3/1990 | Germany . | |
| 1426594 | 9/1988 | U.S.S.R. | 604/280 |
| 1664306 | 7/1991 | U.S.S.R. | 128/DIG. 25 |
| 1088403 | 1/1966 | United Kingdom . | |

*Primary Examiner*—C. Fred Rosenbaum
*Assistant Examiner*—Manuel Mendez
*Attorney, Agent, or Firm*—Keil & Weinkauf

[57] ABSTRACT

A pipe-shaped ureter splint of a resilient material which in its position of use is located in the renal pelvis with one of its ends and with the other end in the bladder, wherein on the outside of the end provided for insertion into the bladder a thin-walled, soft, collapsible hose, of one-piece construction at least in its cross-section, is closely attached and projects beyond the front face of this end of the ureter splint, the cross-section of the hose has a shape that is oval, elliptical, or approximately the shape of an elongated rectangle wherein the transitions from the long to the short sides are rounded off, and the hose functions as an anti-backflow valve.

10 Claims, 5 Drawing Sheets

TUBE-SHAPED URETER SPLINT

The invention relates to a pipe-shaped ureter splint of a resilient material, in particular a plastic material, which in its position of use is located in the renal pelvis with one of its ends and with the other end in the bladder, wherein on the outside of the end provided for insertion into the bladder a thin-walled, soft hose, of one-piece at least in its cross section, is closely attached and projects beyond the front face of this end of the ureter splint.

A ureter splint of this type is known from German Published, Non-Examined Patent Application DE-OS 40 28 477. In connection with this, it is furthermore known and can also be taken from the above mentioned reference, that the ureter splint suitably has an impressed curvature (a so-called "memory") on its ends, by means of which these ends are maintained in the renal pelvis as well as in the bladder, so that the ureter splint cannot be inadvertently displaced in its long direction in the ureter. In accordance with German Published, Non-Examined Patent Application DE-OS 40 28 477 it is prevented by means of the ureter splint that with a pressure increase in the bladder the urine is pushed in a reverse direction from the bladder up into the renal pelvis and in this way triggers a functional interference with and damage to the renal tissue. However, the circular cross section of the hose which can be found in this reference here lends it an undesirable stiffness in respect to the intended change of the shape of the hose, which causes a blockage of the end of the ureter splint at the bladder and in this way prevents rising of the urine.

It is furthermore known from German Published, Non-Examined Patent Application DE-OS 35 25 165 to prevent the unwanted rise of urine from the bladder to the renal pelvis by means of a check valve in the form of a foil valve. In this case the foil valve consists of two flat, thin-walled foils which are glued or welded together along their lateral edges. The disadvantage here is that incrustations form on the inside in the corners next to the welded places. The above mentioned welds and the interior corners existing between them prevent the tight application of such a check valve to the outside of the ureter splint, or at least make it more difficult. Production of such a foil valve entails greater expense in comparison with the production of a hose which per se is of one piece. In addition, such weld seams can become leaky under disadvantageous conditions. Furthermore, such an arrangement does not meet the preamble of claim 1.

Initially, it is the object of the invention to improve an arrangement in accordance with German Published, Non-Examined Patent Application DE-OS 40 28 477 in such a way that, even with a very small increase of pressure in the interior of the bladder, rising of the urine is prevented with the aid of the hose.

On the basis of a ureter splint in accordance with the preamble of claim 1, the features of the characteristics of claim 1 are initially provided to attain this object. In contrast with a hose with a circular cross section, with the layout of the cross section in that way there is, on the one hand, the advantage of decreased production costs and great stability of a one-piece hose which therefore is assuredly leakproof, combined with the advantage that, because of the non-circularity of the cross section of such a hose, it collapses already under a small pressure difference and in this way causes the sealing of the ureter splint against penetration by urine. Claims 2 and 3 represent preferred embodiments of claim 1. The above mentioned pressure difference is generated in that, in the course of a pressure increase in the bladder, a minimal amount of urine flows through the ureter splint towards the kidneys. This causes a pressure difference between the interior lumen of the ureter and the bladder. This pressure difference causes the hose (also called anti-reflux hose) to be placed in front of the openings on the bladder side, in particular the interior lumen of the ureter splint, and in this way prevents further entry of urine into the ureter splint and thus into the renal pelvis.

Starting with the preamble of claim 4, which is coordinated with claim 1, the previously mentioned object can also be attained by the teachings of the characteristics of claim 4. Here, during the above mentioned increase in interior pressure, the hose folds together, looking in its long extension, in accordance with its respectively impressed shape. This results in the hose walls coming to rest against each other and also against the outlet end of the interior lumen of the ureter splint oriented toward the bladder side. In this case, sealing of the end of the ureter splint facing the bladder side against rising of the urine is also accomplished at a very small pressure rise in the bladder interior. This advantage can already be achieved in principle with a hose with a circular cross section. However, it is a preferred embodiment of the invention if, in accordance with claim 9, the teachings of claims 1 and 4 are combined, wherein the position of the long axis of non-circular cross section is such that thereby the folding on top of each other and sealing of the wall sections of the hose, which are zig-zag-shaped, helically-shaped, corkscrew-shaped or have changing cross sections, in case of a pressure rise in the interior of the bladder is made easier.

The characteristics of claims 6, 10 and 11, although known per se from German Published, Non-Examined Patent Application DE-OS 40 28 477, represent advantageous characteristics within the scope of the instant invention.

The characteristics of claim 7 allow the insertion of a guide in an arrangement in accordance with claim 4.

Finally the principle of the invention can also be attained by the teaching of claim 8, which is coordinated with claims 1 and 4 and their dependent claims.

Further advantages and characteristics of the invention ensue from the following description and the associated drawings of embodiment options in accordance with the invention.

Figure 1:
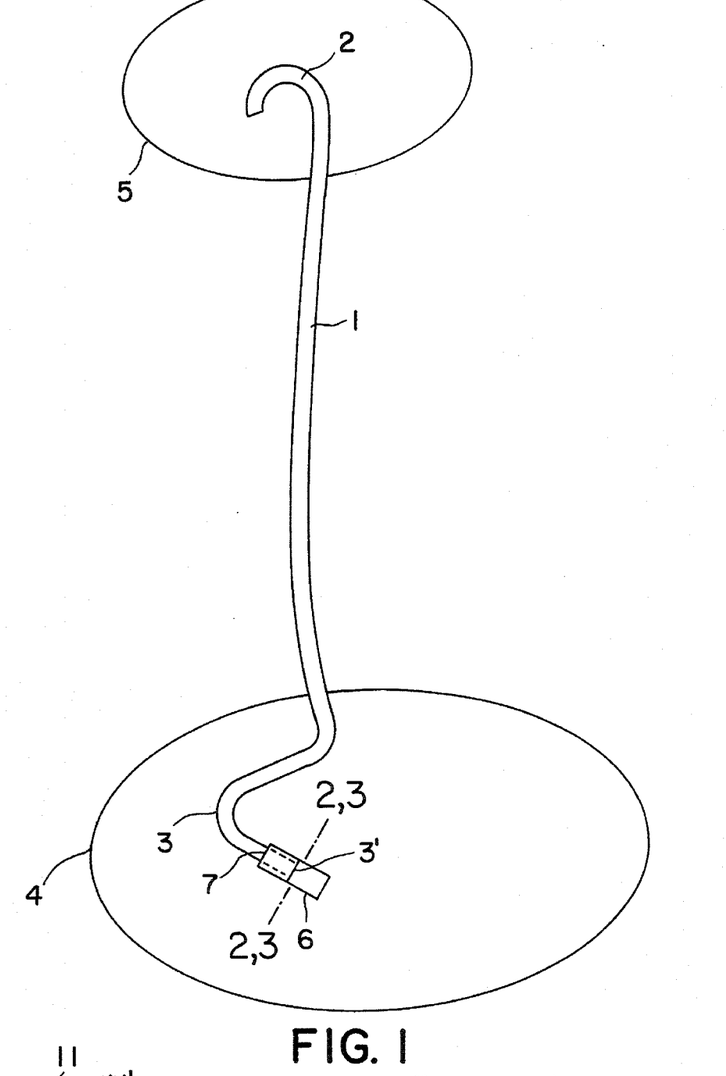
FIG. 1 illustrates a first embodiment of the invention and at the same time the basic arrangement of such a ureter splint.

FIG. 1 basically shows a ureter splint 1 with an end 2 on the kidney side and an end 3 on the bladder side, which as a rule are provided with an impressed curvature (so-called "memory"). After insertion of the ureter splint into the bladder 4 and from there through a ureter, not shown, into the pelvis of the kidney 5, the curved ends 2, 3 maintain the ureter splint 1 in this working position. The end 3 towards the bladder is provided with a thin-walled soft hose 6 which, when the pressure in the bladder rises, folds together in such a way that it prevents the rising of urine contained in the bladder 4 through the ureter splint 1 into the kidney. Several possible ways of an embodiment of this hose are described below. In accordance with FIG. 1, the hose 6 can be oriented obliquely downward from the end 3. However, it can also have another direction.

The hose 6 is of one piece at least in its cross section, but preferably also at the same time over its length. It is pushed on the end 3 of the ureter splint 1 oriented toward the bladder and with its circumference in accordance with reference numeral 7 is tightly fixed on the exterior of the ureter splint 1 [sic], for example by gluing, welding, in particular heat welding. In accordance with the section line 2,3—2,3 the hose 6 has a non-circular cross section which, for example, may be oval or elliptical (FIG. 2) or, in accordance with FIG. 3 is elongated and has the approximate shape of an elongated rectangle. The transition edges 8 from the long sides 9 to the short sides 10 of the cross section are rounded for reasons of manufacturing. Because of the plasticity and possibly the elasticity of the hose material it is possible to push the hose 6 with its non-circular cross section over even the ureter splint with its round cross section and it can be fastened on it in accordance with the explanation of reference numeral 7.

Figure 2:
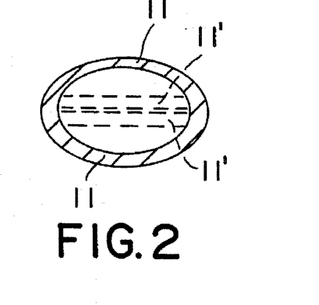
FIGS. 2 and 3 show different embodiments of the invention in a section along line 2,3—2,3 in FIG. 1.
Figure 3:
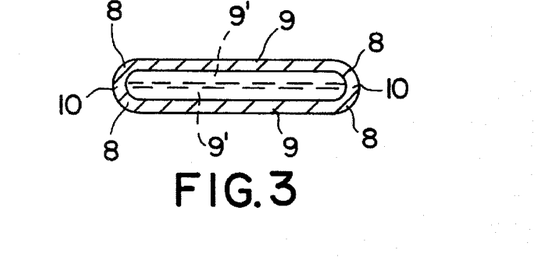

If the bladder is filled with urine to the extent that the pressure generated in it could push the urine upward through the ureter splint, the previously described pressure difference causes the collapse of the hose in such a way that the wails 9 in FIG. 3 and the corresponding long walls 11 of the cross section of FIG. 2, rest sealingly against each other, as indicated by dashed lines numbered 9', 11'. In this way the harmful rising of urine into the renal pelvis is prevented. With the desired normal behavior, on the other hand, the urine is removed from the bladder by the patient. The previously mentioned pressure difference does not occur and the hose 6 is open.

Figure 4:
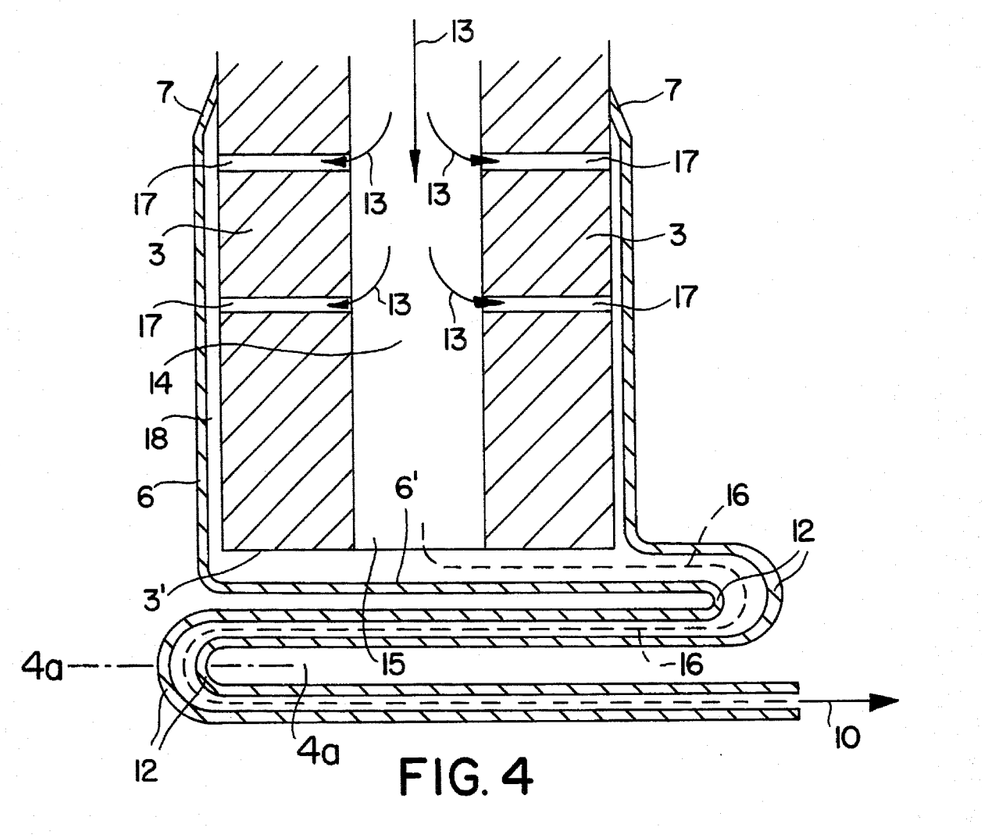
FIG. 4 illustrates a further embodiment of the invention in a sectional view and in the sealing position.
Figure 5:
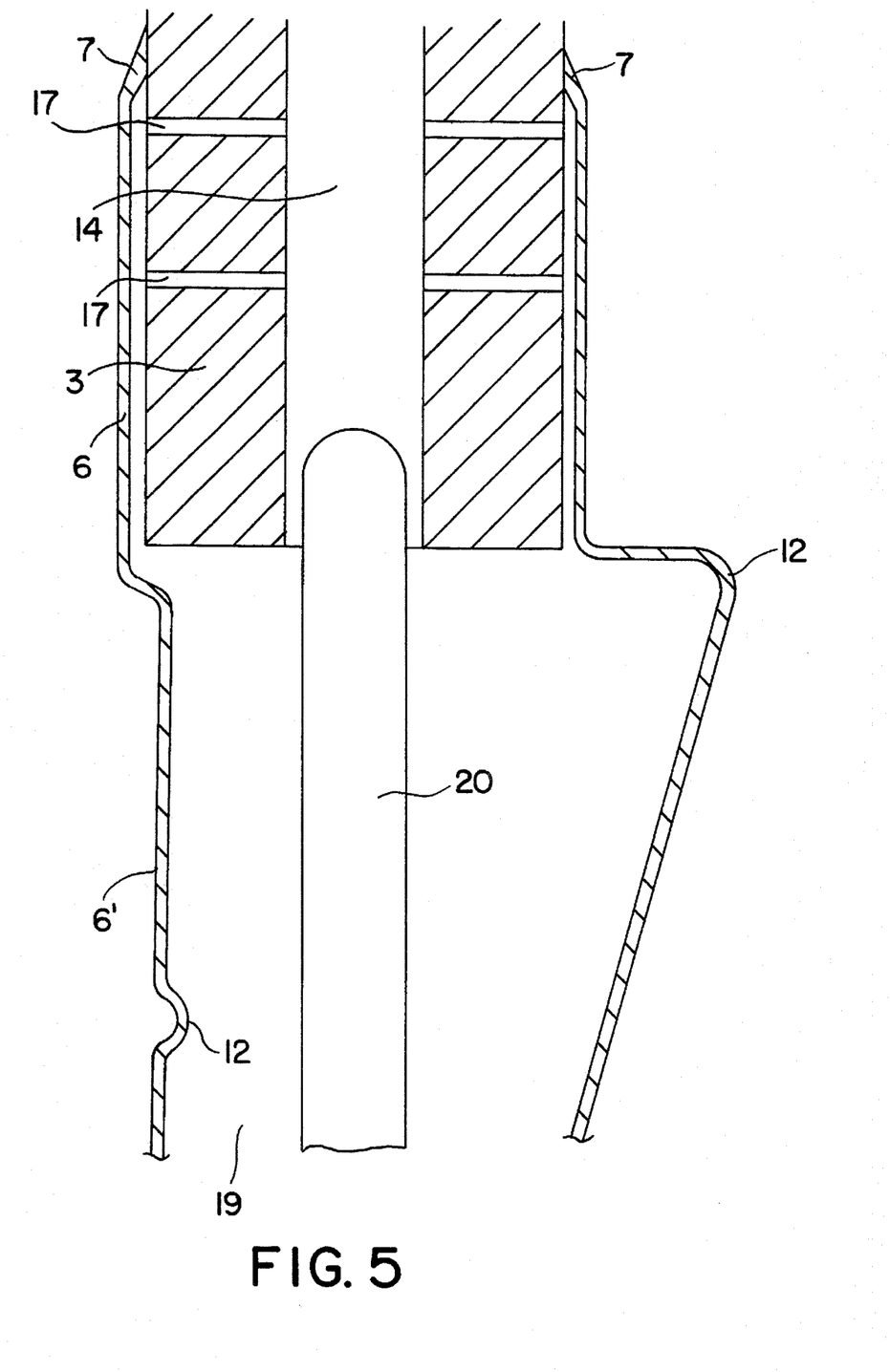
FIG. 5 is the embodiment of FIG. 4 in the open position, also in section.

The exemplary embodiment of FIGS. 4 and 5 shows a portion of the ureter splint 1 with the end 3 oriented toward the bladder and a hose 6, which in accordance with reference numeral 7 is also disposed tightly on the exterior of the ureter splint 1 (see above). The object of the invention, to provide a block of the rise of the urine in the ureter splint even at very small pressure increases in the bladder here has, as in the exemplary embodiment of FIG. 1, initially been attained in that on the one hand the hose 8 projects beyond the front face 3' of the end of the ureter splint oriented toward the bladder and that, on the other hand, it has pre-impressed bends 12 such that it maintains this impressed zig-zag shape. In this case the areas of the hose forming the "zig-zag" shape, which extend horizontally in FIG. 4 (see, for example, reference numeral 6') have a defined distance from each other and also from the front face 3' of the ureter splint. The urine can run off in accordance with the arrow 13 from the renal pelvis through the lumen 14 of the ureter splint downward through the lumen opening 15 and from there, as indicated by the arrow 18, into the bladder. Furthermore, drainage channels 17 can be provided in the wall of the ureter splint, namely in the area between the contact place 7 of the hose 6 and the front face 3', which connect the lumen 14 with a narrow, hollow-cylindrical chamber 18 between the interior surface of the hose 6 and the exterior surface of the ureter splint 1. In this way the urine flowing in accordance with reference numeral 13 from the kidneys can also run off through these drainage channels and the hollow-cylindrical chamber 18. If the previously described increase of the interior pressure now occurs and, along with it a rise of the urine opposite the direction of the arrow 13, which would endanger the patient, the pressure difference being generated causes, on the one hand, that the hose sections (for example reference numeral 6') which are horizontal in FIG. 4 come to rest against each other and particularly against the front face 3' of the end 3 of the ureter splint oriented towards the bladder. Furthermore, this pressure difference causes the hose 6 to come to rest on the outwardly directed openings of the drainage channels 17 and to close them off, too. In this way the dreaded rising of the urine is prevented.

The previously described drainage channels 17 and the provision of the hollow-cylindrical chamber 18 are not absolutely necessary in this embodiment of the invention, but they have the described advantages. The drainage channels 17 and the hollow-cylindrical chamber 18 can also be provided in the embodiment of FIG. 1. In the case of an non-circular cross section of the hose it is recommended to have its long side L (see the explanation of FIG. 4a further down) extend vertically to the drainage channels 17. Thus, the long sides of the hose cross section are located opposite the openings of the drainage channels 17 toward the outside, because of which the application of these hose sides against the exterior of the ureter splint is made correspondingly easier. It also should be noted here that the cross section of the ureter splint is circular, but that the hose which is non-circular in cross section, for example elongated, can be brought without problems into a corresponding, approximately circular cross section for pushing it over the ureter splint end 3 and for fastening it at the point 7.

Furthermore, the embodiment in accordance with FIG. 4 makes it possible, by unfolding or pulling apart of the hose section which in FIG. 4 extend in a zig-zag fashion, while overcoming the force of the impressed "memory", for this hose 6, 6' of FIG. 5 to form a hollow chamber 19, through which it is possible to insert a guide 20 into the lumen 14 of the ureter splint 1. Such a guide is required for inserting the ureter splint into the ureter and to extend it further into the position of its ends 2, 3, shown in FIG. 1, while overcoming the pre-impressed curvatures. As soon as the ureter splint has assumed the end position shown in FIG. 1, the guide 20 is pulled out and the ureter splint ends 2, 3 assume their pre-impressed position, i.e. the position shown in FIG. 1.

Figure 4A:
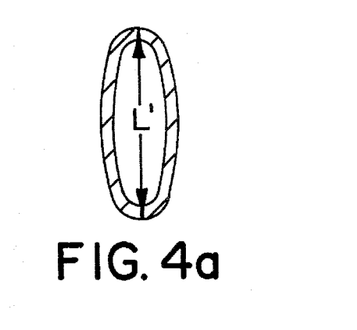
FIG. 4a is a section along the line 4a—4a in FIG. 4.
Figures 6, 7:
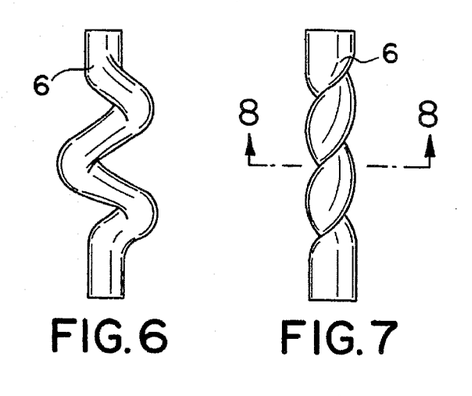
FIG. 6 illustrates a further embodiment of the invention in a lateral view.
FIG. 7 illustrates a still further embodiment of the invention, also in a lateral view.
Figure 8:
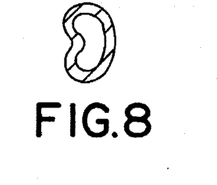
FIG. 8 shows a section along the line 8—8 of FIG. 7.

The teachings of the embodiment in accordance with FIGS. 4 and 5 can be advantageously combined with the teaching of giving the hose 8 a non-circular cross section. This is shown in FIG. 4a, which constitutes a section along the line 4a—4a of FIG. 4. In this case the position of the long axis L of the cross section has been selected to be such that it extends parallel to the buckling or bending line of the hose, preferably coincides with it. When overpressure is generated, this makes the separation of the hose walls and the attachment to the front face 3' of the upper hose section 6', shown in FIG. 4, easier It is also possible to impress a cork-screw-like (FIG. 6) or helix-like configuration (FIG. 7) onto the hose 6. When an overpressure and the above mentioned pressure difference are generated, the turns of the "cork screw" or the walls of the helix (in this connection see the cross section 8—8 in FIG. 8) also correspondingly fold themselves against each other and seal. In these exemplary embodiments the fastening and disposition of the hose on the ureter splint can also be such as shown in FIGS. 4 and 5. In FIGS. 6 and 7 the cross section of the hose is preferably oval or elongated, as also shown in FIG. 8.

Incidentally, the teachings in accordance with FIGS. 4 to 8 for providing the hose with a pre-impressed or impressed shape or curvature in the sense of a "memory", can only be realized with difficulty or not at all in a check valve of two foils welded together in accordance with the above discussed German Published, Non-Examined Patent Application DE-OS 35 25 165, because the laterally welded foil edges prevent this or at least hamper this in actuality.

Figure 9:
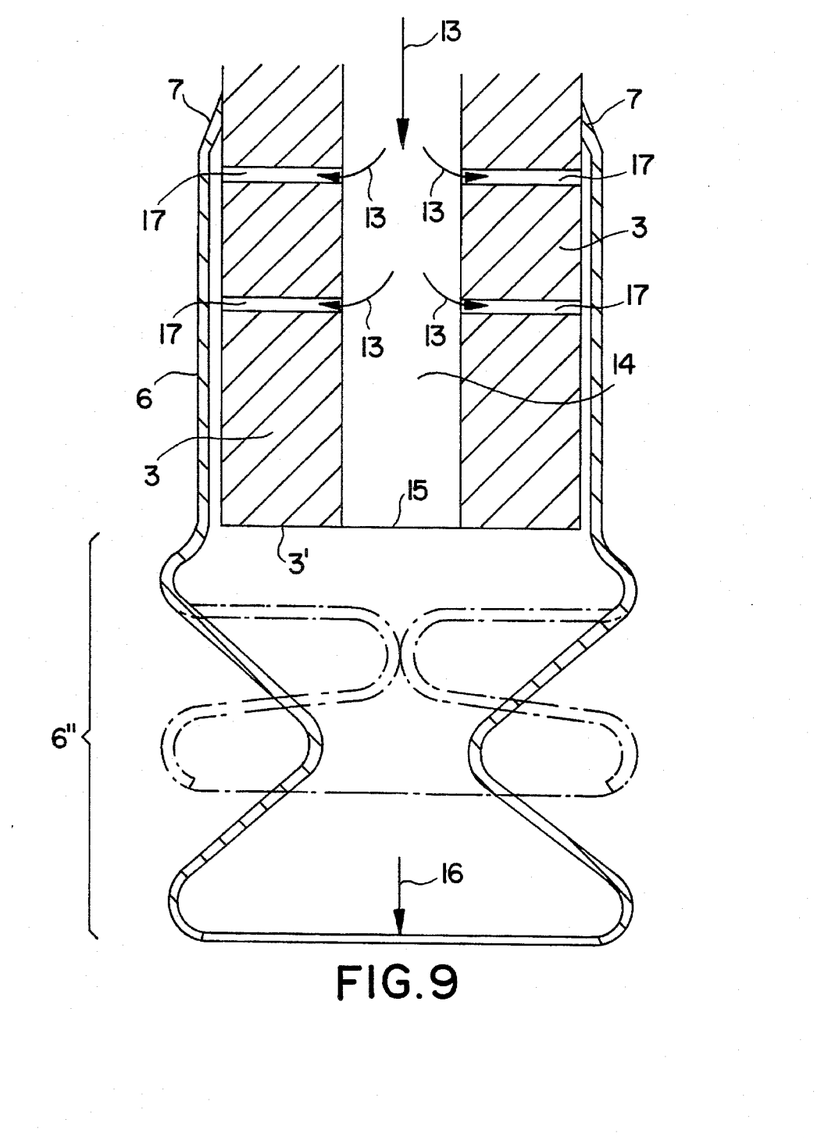
FIG. 9 illustrates a yet further embodiment of the invention, also in a sectional view.

In the embodiment in accordance with FIG. 9, in the area 6" projecting beyond the front face 3', the hose 6 is provided with different diameters which fold against each other under an appropriately high interior pressure in the bladder and take up the approximate position shown in dashed lines, in which they seal the opening 15 of the lumen 14. The bulges achieved by this can also have the shape of a so-called hour glass. At the same time, the hose is sealingly pressed against the outlet openings of the drainage channels 17 in the area 6" in this embodiment, too. The above mentioned shape of the hose in the area 6" is also pre-impressed during manufacture, i.e. it has a so-called "memory". In the normal situation, i.e. with sufficient run-off of urine from the bladder, the memory causes a shaping of the hose which permits flow of urine from the kidneys in the direction of the arrows 13, 16 into the bladder. Something similar to this applies (not shown in detail) for the variants in accordance with FIGS. 6 to 8.

Figure 10:
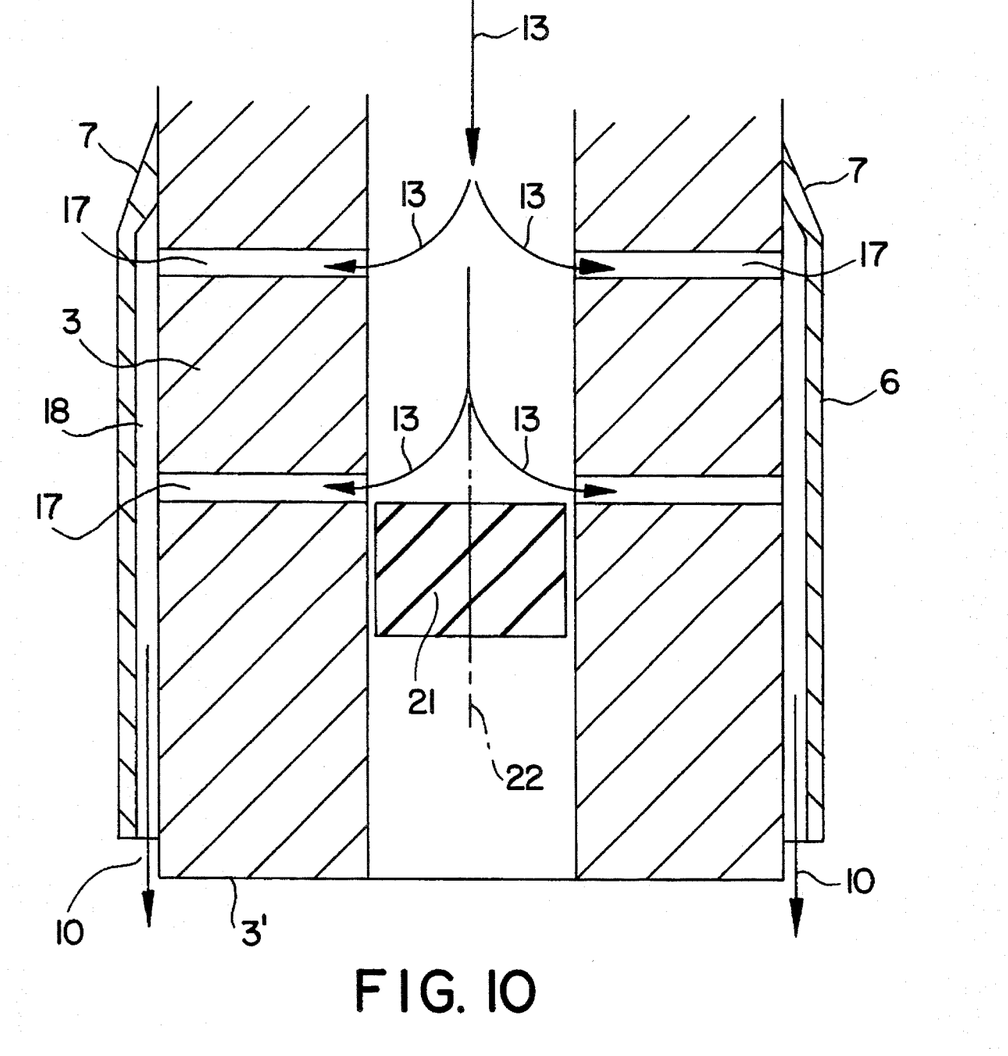
FIG. 10 illustrates a still further embodiment of the invention, also in a sectional view.

The object of the invention can also be attained with an embodiment in accordance with FIG. 10. In this case the hose 6 is also tightly connected at 7 with the ureter splint 1 [sic]. A stopper 21 is located in the lower area of the end 3 of the ureter splint 1 oriented towards the bladder. Drainage channels 17 are provided between it and the sealed connection 7 of the hose, as already previously explained. In addition, the inside of the hose 6 has a defined distance from the exterior surface of the ureter splint 1 [sic], so that here, too, the hollow-cylindrical chamber 18 is provided. The urine coming from the kidneys flows through the drainage channels 17 in accordance with the drawn-in arrows 13 and from there through the cylindrical hollow chamber 18 to the bladder in accordance with the arrows 16. A flow of urine through the lumen is prevented by the stopper 21. However, on the other hand this stopper 21 also prevents a flow of urine opposite the direction of the arrows 13 back into the kidneys as long as an appropriate overpressure acts on the urine in the bladder. Here, too, this overpressure causes the hose 6 to be pressed against the exterior of the ureter splint 1 [sic] and against the openings of the drainage channels 17, so that urine cannot reach the kidneys through these.

The stopper 21 is preferably made of an elastic, foam rubber-like material. On its central longitudinal axis 22 it has a perforation, not shown in the drawings, through which a guide (see reference numeral 20 in FIG. 5) can be inserted to allow the insertion, described above, of the ureter splint into the position in accordance with FIG. 1. After removal of the guide, the above mentioned bore closes automatically because of the inherent elasticity of the material of the stopper 21. In the exemplary embodiment of FIG. 10, the drainage channels 17 and the hollow-cylindrical annular chamber 18 are required to assure flow-off of the urine, as described. However, it is not necessary with the embodiment of FIG. 10 that the hose 6 project beyond the front face 3' of the ureter splint 1 [sic]. It is important here that the material of the stopper 21 permits a guide to pass through its central perforation area, but that the perforation area closes again after its removal because of its elasticity and prevents the passage of urine.

All characteristics illustrated and described, as well as their combinations with each other, are important for the invention, unless expressly designated as being known.

I claim:

1. A pipe-shaped ureter splint of a resilient material, in particular a plastic material, which in its position of use is located in the renal pelvis with one of its ends and with the other end in the bladder, wherein on the outside of the end provided for insertion into the bladder a thin-walled, soft, collapsible hose, of one-piece construction at least in its cross-section, is closely attached and projects beyond the front face of this end of the ureter splint, characterized in that the cross-section of the hose has a shape that is oval, elliptical, or approximately the shape of an elongated rectangle wherein the transitions from the long to the short sides are rounded off, and the hose functions as an anti-backflow valve.

2. A ureter splint in accordance with claim 1, wherein the cross-section of the hose is chosen from one of the group composed of oval, elliptical, and an elongated rectangle wherein the corners are at least somewhat rounded off, the entire invention characterized in that in the end of the ureter splint oriented towards the bladder, drainage channels are provided, located in the area between the tight application of the hose on the ureter splint and the front face of the end of the ureter splint oriented towards the bladder, which channels lead outward from the lumen of the splint to a narrow gap having two ends, said gap located between the exterior surface of the ureter splint and the interior surface of the hose, which gap is blocked at one end by the tight application of the hose on the ureter splint, and opens at its other end into the interior space of the hose.

3. A pipe-shaped ureter splint of a resilient material, in particular a plastic material, which in its position of use is located in the renal pelvis with one of its ends and with the other end in the bladder, wherein on the outside of the end provided for insertion into the bladder a thin-walled, soft, collapsible hose, of one-piece construction at least in its cross-section, is closely attached and projects beyond the front face of this end of the ureter splint, characterized in that the portion of the hose projecting beyond the front face of the end of the ureter splint oriented toward the bladder side is formed with a pre-impressed shape memory giving the hose, when relaxed, a zig-zag, helical or corkscrew shape, or else it is formed so that its diameter increases and then again decreases along the projecting hose section.

4. A ureter splint in accordance with claim 3, characterized in that the hose section, provided with a pre-impressed convoluted or meandering shape memory, can be stretched out sufficiently far that it is possible to insert a guide into the lumen through it.

5. A ureter splint according to claim 3, wherein the cross-section of the hose is chosen from one of the group composed of oval, elliptical, and an elongated rectangle whose corners are at least somewhat rounded off.

6. A ureter splint in accordance with claim 3, characterized in that in the end of the ureter splint oriented towards the bladder, drainage channels are provided, located in the area between the tight application of the hose on the ureter splint and the front face of the end of the ureter splint oriented towards the bladder, which channels lead outward from the lumen of the splint to a narrow gap having two ends, said gap located between the exterior surface of the ureter splint and the interior surface of the hose, which gap is blocked at one end by the tight application of the hose on the ureter splint, and opens at its other end into the interior space of the hose.

7. A ureter splint in accordance with claim 5, characterized in that in the end of the ureter splint oriented towards the bladder, drainage channels are provided, located in the area between the tight application of the hose on the ureter splint and the front face of the end of the ureter splint oriented towards the bladder, which channels lead outward from the lumen of the splint to a narrow gap having two ends, said gap located between the exterior surface of the ureter splint and the interior surface of the hose, which gap is blocked at one end by the tight application of the hose on the ureter splint, and opens at its other end into the interior space of the hose.

8. A ureter splint according to claim 5, characterized in that the hose section, provided with a pre-impressed convoluted or meandering shape memory, can be stretched out sufficiently far that it is possible to insert a guide into the lumen through it.

9. A ureter splint according to claim 2, characterized in that the hose section, provided with a pre-impressed convoluted or meandering shape memory, can be stretched out sufficiently far that it is possible to insert a guide into the lumen through it.

10. A pipe-shaped ureter splint of a resilient material, in particular a plastic material, which in its position of use is located in the renal pelvis with one of its ends and with the other end in the bladder, wherein on the outside of the end provided for insertion into the bladder a thin-walled, soft, collapsible hose, of one-piece at least in its cross section, is closely attached and projects beyond the front face of this end of the ureter splint and functions as an anti-backflow valve, said ureter splint characterized in that in the end of the ureter splint oriented towards the bladder, drainage channels are provided, located in the area between the tight application of the hose on the ureter splint and the front face of the end of the ureter splint oriented towards the bladder, which channels lead outward from the lumen of the splint to a narrow gap having two ends, said gap located between the exterior surface of the ureter splint and the interior surface of the hose, which gap is blocked at one end by the tight application of the hose on the ureter splint, and opens at its other end into the interior space of the hose, wherein further in the area towards the bladder between the drainage channels and the face end of the ureter splint oriented towards the bladder, the lumen of the ureter splint is closed by means of a stopper which has a perforation in its center and which consists of an elastic material which permits the passage of a guide through the perforation area allowing the guide to protrude and straighten and direct the ureter splint, but which central perforation of the stopper closes upon removal of the guide and in this way seals the lumen of the ureter splint against the passage of urine.

* * * * *

UNITED STATES PATENT AND TRADEMARK OFFICE
CERTIFICATE OF CORRECTION

PATENT NO.: 5,531,718

DATED: July 2, 1996

INVENTOR(S): Hans SACHSE

It is certified that error appears in the above-identified patent and that said Letters Patent is hereby corrected as shown below:

On the cover page, item [30], "42 36 571.6" should read
--P 42 36 571.6--.

Signed and Sealed this

Tenth Day of September, 1996

Attest:

Attesting Officer

BRUCE LEHMAN

Commissioner of Patents and Trademarks